US00PP09714P

United States Patent [19]

van Rosmalen

[11] Patent Number: Plant 9,714

[45] Date of Patent: Nov. 26, 1996

[54] ANTHURIUM PLANT NAMED 'TOSCANE'

[75] Inventor: N. A. M. van Rosmalen, The Hague, Netherlands

[73] Assignee: Nic Van Der Knaap Anthuriumselecties B.V., Bleiswijk, Netherlands

[21] Appl. No.: 516,558

[22] Filed: Aug. 18, 1995

[51] Int. Cl.[6] ..... A01H 5/00

[52] U.S. Cl. ..... Plt./88.1

[58] Field of Search ..... Plt./88.1

*Primary Examiner*—James R. Feyrer

*Attorney, Agent, or Firm*—Foley & Lardner

[57] ABSTRACT

'Toscane' can be used as a decorative pot plant that flowers early and abundantly. The plant can be sold in different sizes from approximately 40 cm to 80 cm in height. The plant produces abundant flowers that enlarge in size as the plant becomes bigger. The decorative leaves are glossy, dark green, coriaceous and extremely durable. 'Toscane' produces bright, long-lived and large flowers that are held above the foliage. The heart-shaped flowers maintain their original red color as they mature.

4 Drawing Sheets

INTRODUCTION

'Toscane' is a new and distinct cultivar of Anthurium, botanically known as *Anthurium andreanum* L. The new cultivar is a product of a planned breeding program, and was obtained from a cross made during such a program in Bleiswijk, The Netherlands, in 1989. The female or seed parent was a proprietary red-flowering Anthurium pot plant having selection number 82-00-18. The male or pollen parent was a proprietary red flowering Anthurium pot plant with small leaves having, selection number 89-00-110. 'Toscane' was discovered and selected as a flowering plant within the progeny of the stated cross by N. A. M. van Rosmalen on February 1989 in a controlled environment in a glasshouse in Bleiswijk. Subsequent asexual reproduction by tissue culture at the same location has demonstrated that the combination of characteristics as herein disclosed for the new cultivar are firmly fixed and are retained through successive generations of asexual reproduction.

The following observations, measurements and values describe plants grown in Bleiswijk, The Netherlands, under greenhouse conditions which closely approximate those generally used in horticultural practice. Color references are made to The Royal Horticultural Society (R.H.S.) Colour Chart, except where general color terms of ordinary significance are used. The color references are approximate, as color depends to a degree on horticultural practices such as light level and degree of fertilization, among others. The color values were determined between 11:30 a.m. and 2:00 p.m. on Feb. 8, 1995 under 10.000 lux natural light in a glasshouse in Bleiswijk. The phenotype may vary significantly when grown under different conditions of temperature, light or other determining factors, without a change in genotype of the plant.

The following traits have been repeatedly observed and in combination distinguish 'Toscane' as a new and distinct cultivar:

1. The plant can be sold at different stages of growth because the plant flowers early and fully. Because 'Toscane' flowers early and fully, the plant can be sold at different stages, from a mini-type of 40 cm in height, to a big plant that is 80 cm in height.

2. The penducle is long and erect and therefore the flowers are held well above the foliage.

3. The plant habit is full due to shoot formation.

4. The leaves are dark green, glossy and durable with light green primary veins.

5. The flowers are very durable and maintain their original red color as they mature. These qualities lead to a rich flowering and a decorative pot plant.

6. The flowers are large in relation to the leaf blades and therefore the ratio of leaf to flower size is excellent.

DESCRIPTION OF THE PHOTOGRAPHIC DRAWINGS

The accompanying photographs, taken in Bleiswijk, The Netherlands, show typical 'Toscane' specimens.

Sheet 1 is a sideview of 'Toscane' showing the flowers held well above the leaf canopy.

Sheet 2 is a close-up of a 'Toscane' flower showing that the angle between the spathe and spadix is approximately 90 degrees.

Sheet 3 is a close-up of 'Toscane' flowers at three different development stages. The flower on the right is the youngest and the one on the left with the green spadix is the oldest. As the flower matures the spathe color does not fade.

Sheet 4 is a close-up of a leaf blade showing its dark green color with a shiny surface and light green veins.

DETAILED DESCRIPTION

Classification:

*Botanical.*—*Anthurium andreanum* L., cv 'Toscane.'

*Commercial.*—'Toscane'.

Parentage: Seedling of a cross between selection numbers 82-00-18 (female) × 89-00-110 (male). Selections 82-00-18 and 89-00-110 are red pot plants.

Propagation:

Asexual multiplication is by means of tissue culture and all propagations that flowered have been true to the original type in plant and flower characteristics.

Plant description:

*Plant.*—Approximately 65–70 weeks following division 'Toscane' will reach a mature size of approximately 30 cm to 60 cm in height and approximately 35 cm to 55 cm in width in a 14 cm pot. However, 'Toscane' can be easily grown to a larger size for example 80 cm in height, when it is placed in a larger pot.

*Leaves.*—Form: The leaf blade is elliptical-cordate with an acute tip and a cordate base. The leaf blade angle with the petiole is between 120 and 140 degrees. Size: 'Toscane' can be sold in different age classes and leaf blades enlarge as the plant ages. 'Toscane' also produces some axillary shoots with small leaf blades. As a result, a wide range in leaf blade length and width is found on each plant. The minimum leaf blade length is approximately 5 cm and the maximum leaf blade length is approximately 30 cm. The minimum leaf blade width is approximately 3 cm and the maximum leaf blade width is approximately 20 cm. Texture: The leaf blades are leathery and thick. The mature leaf blades are weakly cupped. Veins: The midvein and primary veins (radiate out from juncture of petiole and leaf) protrude at the underside of the leaf blade. The light green color (upper surface): R.H.S. 144A and lower surface: R.H.S. 144B) of the midvein and primary veins (approximately 6 to 8) contrast with the dark green color of the upper surface of the leaf blade. Color: The exact color of the upper surface of the leaf blades is not available on the R.H.S. color card but R.H.S. 147A resembles it most closely. The leaf blade lower surface is light green (R.H.S. 146B). Lobes: A leaf blade has two lobes extending past the petiole. The distance from petiole/leaf juncture to the highest point on the lobes of mature leaf blades (width 17 cm, length 30 cm) ranges approximately from 7 to 8 cm. Petiole: The color of the petiole is green (R.H.S. 144A). The cross-section of the petiole is round and the diameter is approximately 2 mm to 6 mm. The color of the cataphyls surrounding the petioles is R.H.S. 175A.

*Spathe.*—Buds: The spathe is tightly rolled around the spadix and extrudes from the peduncle sheath. The spathe is fully open at approximately the same time that the peduncle fully elongates. Size: The flattened spathe of a 40 cm tall plant is approximately 6 cm to 7 cm long and approximately 7 cm to 8 cm width. The flattened spathe of a 60 cm tall plant is approximately 7 cm to 8 cm long and approximately 7.5 cm to 8.5 cm wide. The flattened spathe of a 80 cm tall plant is approximately 9 cm to 10 cm long and approximately 10 cm to 11 cm wide. Color: The spathe color was measured in Bleiswijk The Netherlands. When the spathe is just fully open the upper surface is R.H.S. 46A and the lower surface is R.H.S. 47A-B. Mature flowers do not fade immediately but keep their original color for a long time with an upper surface of R.H.S. 46A and a lower surface of R.H.S. 47A-B. The primary veins in the spathe of a mature flower can fade to dark green. Arrangement: The spathe stands almost horizontal on a straight wiry pedicel (peduncle) approximately 6 cm to 15 cm above the foliage. The peduncle cross-section is round and the diameter approximately 2 mm to 6 mm, depending on the age of the plant. The peduncle is erect and it's length depends on the plant-age and ranges from approximately 30 cm to 55 cm. Shape: The spathe is cordate (heart-shaped) with a mucronate tip and a cordate base. The spathe of a just fully opened flower is flat. The lobes of the spathe bend upwards slightly as the flower ages. Flowering time: One small untreated tissue culture plant of approximately 2 cm tall will flower, depending on season, after approximately 16 to 17 months when approximately 3 to 4 blossoms will appear. More blossoms appear a few weeks later so that a full flowering and salable plant can have 6 to 8 red flowers. Smaller blossoms may occur on less mature growth.

*Reproductive organs.*—Size: The spadix measures approximately 6 to 9 cm in height, the same length as that of the spathe. The spadix is a little columnar. The width of a mature spadix that is approximately 9 cm long is approximately 7 to 8 mm at the top and approximately 12 mm to 13 mm at the base. The spadix angle with spathe is approximately 90 degrees. Color: The spadix color was measured in Bleiswijk, The Netherlands. At the time the spathe unrolls the spadix is divided into unripe and ripe portions. The unripe portion at the top-side is yellow (R.H.S. 20A) and the ripe portion at the base-side is white (R.H.S. 159B). As the spadix matures it becomes first fully white and then turns slightly light green (R.H.S. 145A). Stamens: Anthers and filaments are not clearly visible on the spadix. Pollen: Does not appear because the plant is male sterile. Pistil: The same color as described for the spadix. The pistil protrudes from the spadix. Roots: Flesh cream-white roots with smaller hairy laterals. Yellow root-tips. Disease: Unknown.

I claim:

1. A new and distinct Anthurium plan named 'Toscane', as herein described and illustrated.

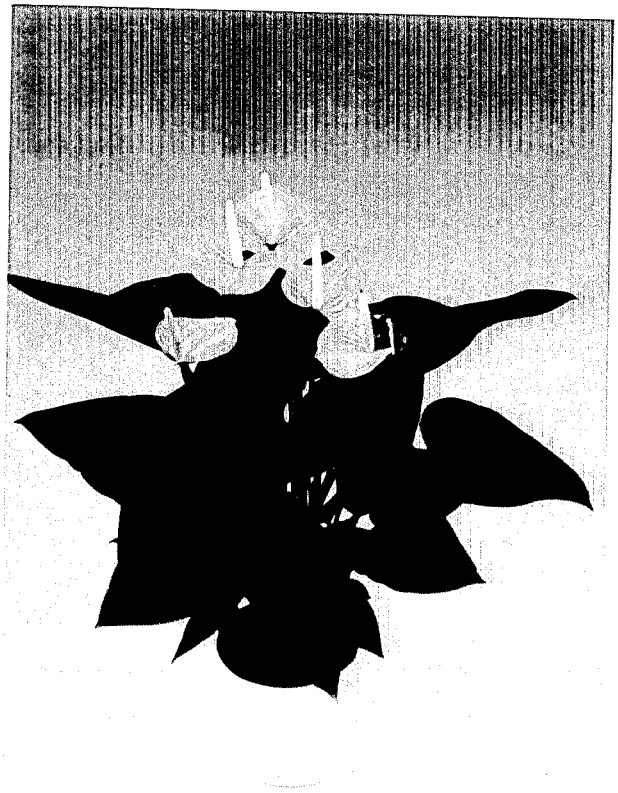

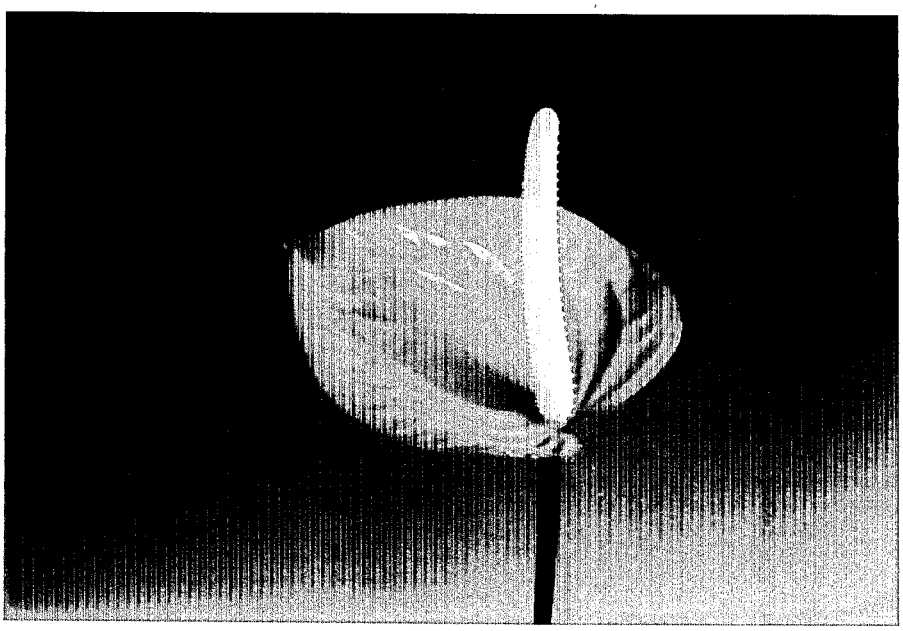

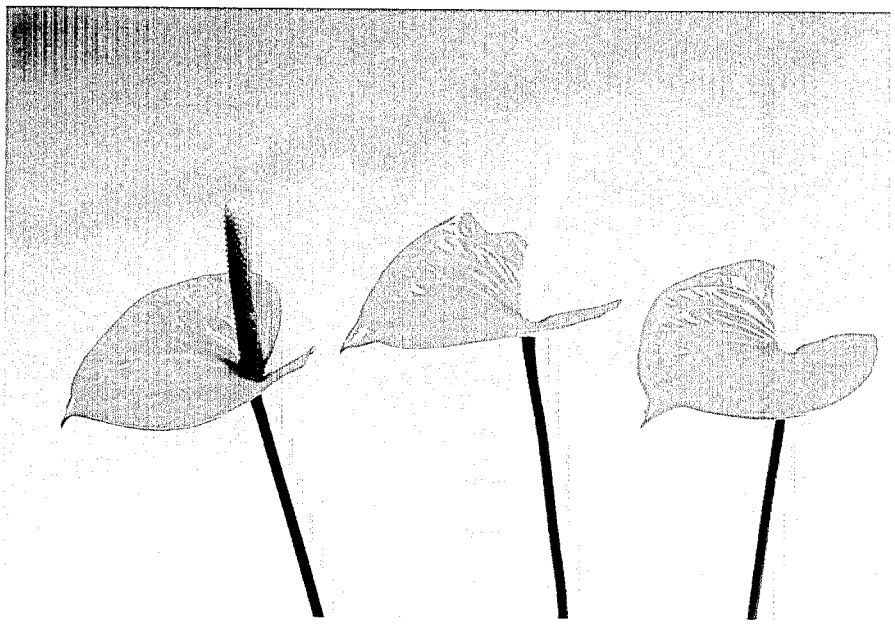

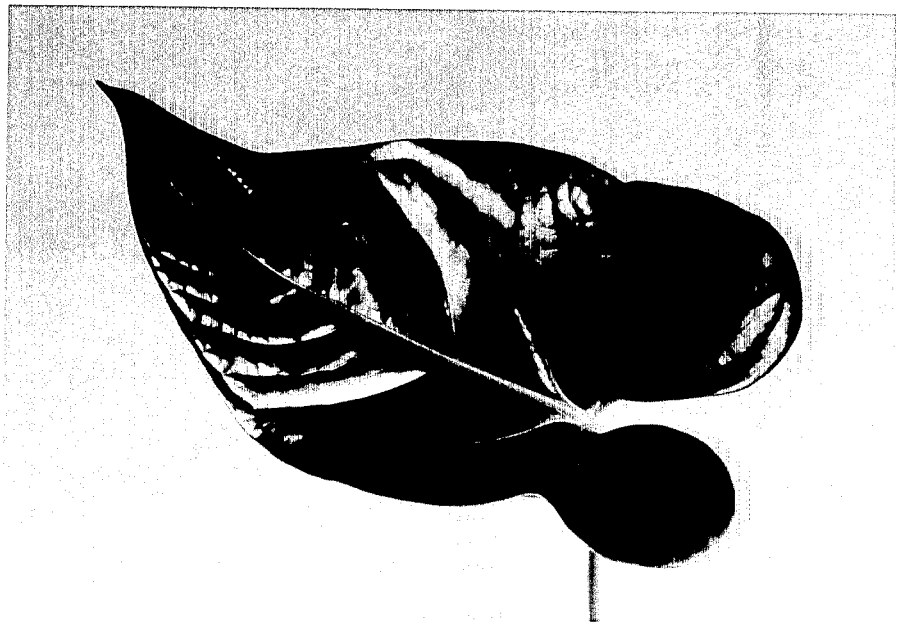

* * * * *